(12) United States Patent
Baxi et al.

(10) Patent No.: US 10,932,677 B2
(45) Date of Patent: Mar. 2, 2021

(54) OPTICAL HEART RATE SENSOR WITH REDUCED POWER

(71) Applicant: Intel Corporation, Santa Clara, CA (US)

(72) Inventors: Amit S. Baxi, Thane (IN); Apoorv Vyas, Bangalore (IN); Sanika Phatak, Pune (IN); Krishna P. Bhat D., Bangalore (IN)

(73) Assignee: Intel Corporation, Santa Clara, CA (US)

( * ) Notice: Subject to any disclaimer, the term of this patent is extended or adjusted under 35 U.S.C. 154(b) by 763 days.

(21) Appl. No.: 15/492,986

(22) Filed: Apr. 20, 2017

(65) Prior Publication Data

US 2018/0303353 A1     Oct. 25, 2018

(51) Int. Cl.

| | |
|---|---|
| *A61B 5/02* | (2006.01) |
| *A61B 5/021* | (2006.01) |
| *A61B 5/0456* | (2006.01) |
| *A61B 5/024* | (2006.01) |
| A61B 5/0404 | (2006.01) |
| A61B 5/0408 | (2006.01) |
| A61B 5/00 | (2006.01) |

(52) U.S. Cl.
CPC ...... *A61B 5/02125* (2013.01); *A61B 5/02416* (2013.01); *A61B 5/0456* (2013.01); *A61B 5/002* (2013.01); *A61B 5/02438* (2013.01); *A61B 5/0404* (2013.01); *A61B 5/04087* (2013.01); *A61B 5/7285* (2013.01); *A61B 2562/0209* (2013.01)

(58) Field of Classification Search
CPC .............. A61B 5/02125; A61B 5/0456; A61B 5/02416; A61B 5/002; A61B 5/0404; A61B 5/04087; A61B 5/7285; A61B 5/02438; A61B 2562/0209
See application file for complete search history.

(56) References Cited

U.S. PATENT DOCUMENTS

2015/0018693 A1* 1/2015 Mestha .............. A61B 5/02427
600/479

* cited by examiner

*Primary Examiner* — Christian Jang
(74) *Attorney, Agent, or Firm* — Schwabe, Williamson & Wyatt, P.C.

(57) ABSTRACT

Methods, systems, and storage media relating to a circulatory health monitor device are disclosed herein. In an embodiment, such a device may be positioned or disposed on and/or in contact with a subject to measure blood pressure and/or heart rate. The device may include one or more electrocardiographic (ECG) signal sensors, one or more photoplethysmographic (PPG) sensors, and a controller. The controller may activate at a low resolution a PPG measurement of the subject in relation to an ECG signal feature to identify a PPG signal feature location or region in the PPG measurement. The controller may further activate at a high resolution PPG measurement of the subject at the PPG signal feature region to identify the PPG signal feature, and may determine blood pressure and/or heart rate therefrom. Other embodiments may be disclosed and/or claimed.

20 Claims, 6 Drawing Sheets

OPTICAL HEART RATE SENSOR WITH REDUCED POWER

FIELD

The present disclosure relates to the field of optical heart rate sensor devices, and in particular, to apparatuses, methods and storage media associated with such devices.

BACKGROUND

A circulatory health monitor device, such as a blood pressure monitor device and/or a heart rate monitor, may be positioned or disposed on and/or in contact with the body of a person or a non-human animal to measure blood pressure and/or heart rate. In embodiments, the health monitor device may include one or more electrocardiographic (ECG) signal sensors, one or more photoplethysmographic (PPG) sensors, and a controller coupled to the one or more ECG signal sensors and the one or more PPG sensors.

The accuracy of Blood Pressure (BP) estimation depends on the accuracy of Pulse Transit Time (PTT) measurement. PTT accuracy, in turn, requires measuring accurately the time interval between R-wave peaks in ECG to the corresponding PPG peak. Similarly, Heart Rate (HR) accuracy is dependent on accurately measuring the time interval between two consecutive PPG peaks. This makes accurate detection of temporal location of PPG peak critical for both PTT and HR. Typically, the PTT value is about 200 milliseconds (ms) at rest. An error of even 1 ms in PTT measurement can cause 1 mmHg error in BP estimation. The maximum permissible error in BP is 5 mmHg, which makes accurate PTT measurement extremely critical.

To achieve PTT accuracy of less than 1 ms, the sampling rate for ECG and PPG signals should be greater than or equal to 1000 Hz, so that the consecutive samples are spaced less than 1 ms apart. This means that the optical LEDs in PPG sensor should be pulsed (illuminated and turned OFF) every 1 ms for each PPG sample measurement. To pick up even a weak PPG signal on dark skin, LEDs must be pulsed at upto 100 mA peak current. But frequent pulsation (1 ms) of LEDs at high peak currents, not only causes significant battery-drain, but also causes significant LED heating, which can result in skin burns. So it is essential to find a way to reduce LED power and heating.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example, and not by way of limitation, in the figures of the accompanying drawings.

DETAILED DESCRIPTION

In the following detailed description, reference is made to the accompanying drawings which form a part hereof wherein like numerals designate like parts throughout, and in which is shown by way of illustrated embodiments that may be practiced. It is to be understood that other embodiments may be utilized and structural or logical changes may be made without departing from the scope of the present disclosure. Therefore, the following detailed description is not to be taken in a limiting sense, and the scope of embodiments is defined by the appended claims and their equivalents.

Various operations may be described as multiple discrete actions or operations in turn, in a manner that is most helpful in understanding the claimed subject matter. However, the order of description should not be construed to imply that the various operations are necessarily order-dependent. In particular, these operations might not be performed in the order of presentation. Operations described may be performed in a different order than the described embodiments. Various additional operations might be performed, or described operations might be omitted in additional embodiments.

The description may use the phrases "in an embodiment", "in an implementation", or in "embodiments" or "implementations", which may each refer to one or more of the same or different embodiments. Furthermore, the terms "comprising," "including," "having," and the like, as used with respect to embodiments of the present disclosure, are synonymous.

As used herein, the term "logic" and "module" may refer to, be part of, or include any or any combination of an Application Specific Integrated Circuit (ASIC), an electronic circuit, a programmable combinatorial circuit (such as field programmable gate arrays (FPGA)) a processor (shared, dedicated, or group) or memory (shared, dedicated, or group) that execute one or more software or firmware programs, or other suitable components that provide the described functionality.

Also, it is noted that example embodiments may be described as a process depicted with a flowchart, a flow diagram, a data flow diagram, a structure diagram, or a block diagram. Although a flowchart may describe the operations as a sequential process, many of the operations may be performed in parallel, concurrently, or simultaneously. In addition, the order of the operations may be re-arranged. A process may be terminated when its operations are completed, but may also have additional steps not included in a figure. A process may correspond to a method, a function, a procedure, a subroutine, a subprogram, and the like. When a process corresponds to a function, its termination may correspond to a return of the function to the calling function a main function.

As disclosed herein, the term "memory" may represent one or more hardware devices for storing data, including random access memory (RAM), magnetic RAM, core memory, read only memory (ROM), magnetic disk storage mediums, optical storage mediums, flash memory devices or other machine readable mediums for storing data. The term "computer-readable medium" may include, but is not limited to, memory, portable or fixed storage devices, optical storage devices, and various other mediums capable of storing, containing or carrying instructions or data.

Furthermore, example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium. A code segment may represent a procedure, a function, a subprogram, a program, a routine, a subroutine, a module, program code, a software package, a class, or any combination of instructions, data structures, program statements, and the like.

As used herein, the term "network element", may be considered synonymous to or referred to as a networked computer, networking hardware, network equipment, router, switch, hub, bridge, gateway, or other like device. The term "network element" may describe a physical computing device of a network with wired or wireless communication links. Furthermore, the term "network element" may describe equipment that provides radio baseband functions for data or voice connectivity between a network and one or more users.

Figure 1:
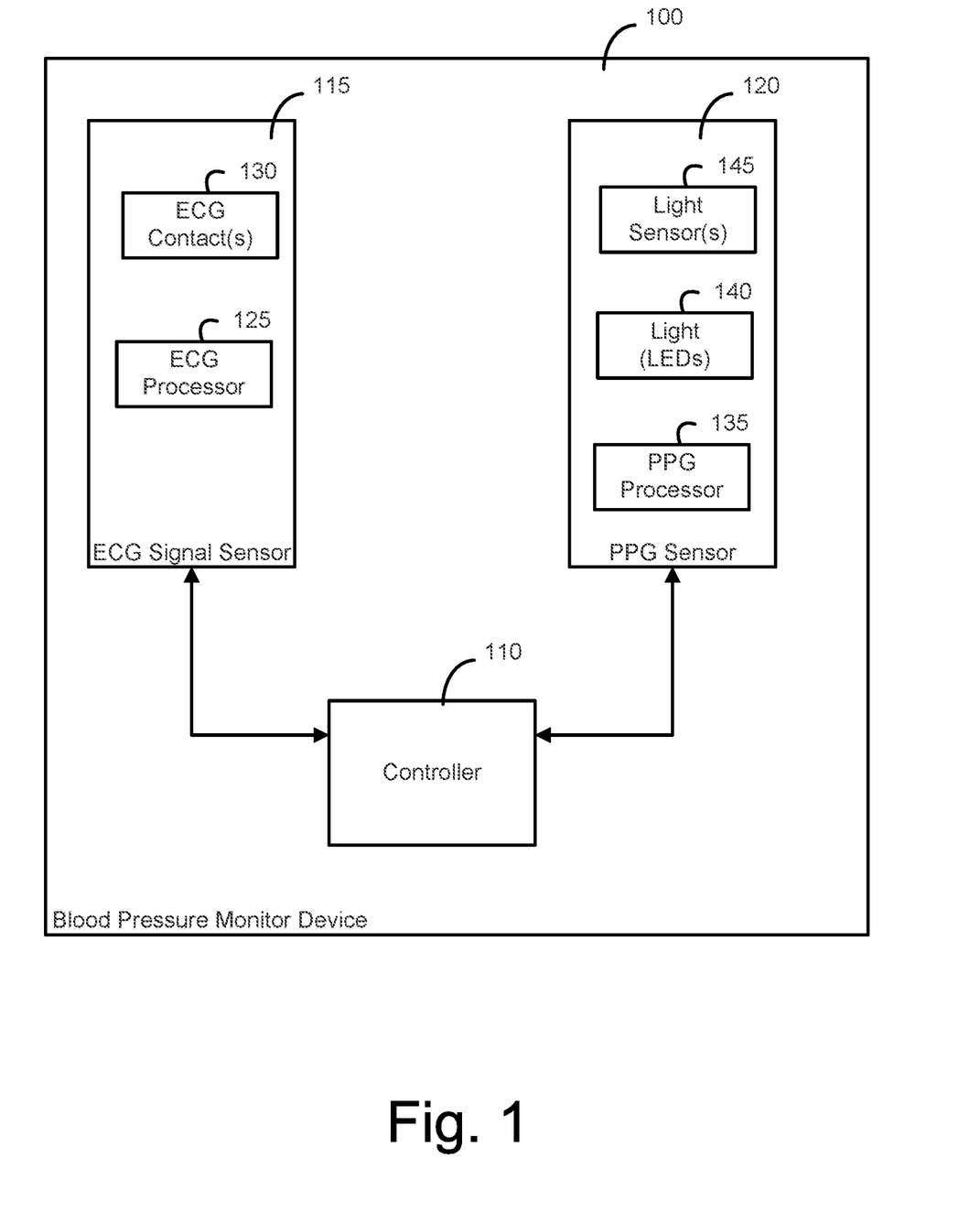
FIG. 1 is a block diagram of a blood pressure monitor device, according to some embodiments.

FIG. 1 is a block diagram of a blood pressure monitor device 100, according to some embodiments. Blood pressure monitor device 100 may be positioned or disposed on and/or in contact with the body of a person or a non-human animal to measure blood pressure. Such a person or non-human animal may be referred to herein as a patient or subject. In some embodiments, monitor device 100 may also and/or alternatively measure heart rate and may additionally and/or alternatively be referred to as heart rate monitor device 100 or, generally, a circulatory health monitor device 100. In embodiments, device 100 may be and/or include a cuffless blood pressure device that may be adhered or otherwise held to a patient's or subject's body (e.g., chest) and so may be a wearable device. In other embodiments, device 100 may be worn on a patient's wrist or on or at another body region.

Blood pressure monitor device 100 may include a controller 110, an electrocardiographic (ECG) signal sensor 115, and a photoplethysmographic (PPG) sensor 120. Controller 110 may be in communication with ECG signal sensor 115 and PPG sensor 120, which may respectively provide and/or obtain ECG and PPG measurements of a subject. ECG signal sensor 115 may include an ECG processor 125 and one or more ECG contacts 130 to be in contact with a subject body to receive one or more ECG signals from the subject. ECG processor 125 may provide an ECG measurement based on one or more ECG signals that may be received from the subject at the one or more ECG contacts 130.

PPG sensor 120 may include a PPG processor 135, and one or more light sources 140 (e.g., one or more LEDs 140, which may be referred to singularly as light source 140 or LED 140) and one or more light sensors 145 to be positioned adjacent or against a subject's body to obtain one or more PPG measurements from the subject. PPG processor 135 may provide a PPG measurement based on light that may be received by one or more light sensors 145 positioned adjacent or against a subject's body from illumination of the subject's body by light source 140. In embodiments, ECG signal sensor 115 and/or PPG sensor 120 may operate in cooperation with or under control of controller 110, and further may provide their respective measurements to controller 110, in accordance with the techniques of the present disclosure, resulting in reduced power requirement. In some embodiments, ECG processor 125 and/or PPG processor 135 may be distinct from controller 110 or may be integral with and/or share, for example, a substrate or die with controller 110. In embodiments, ECG signal sensor 115 and PPG sensor 120 may operate simultaneously. Controller 110, ECG processor 125, and/or PPG processor 135 may be housed or contained in a housing or body that may be supported by a wearable device.

Figure 2:
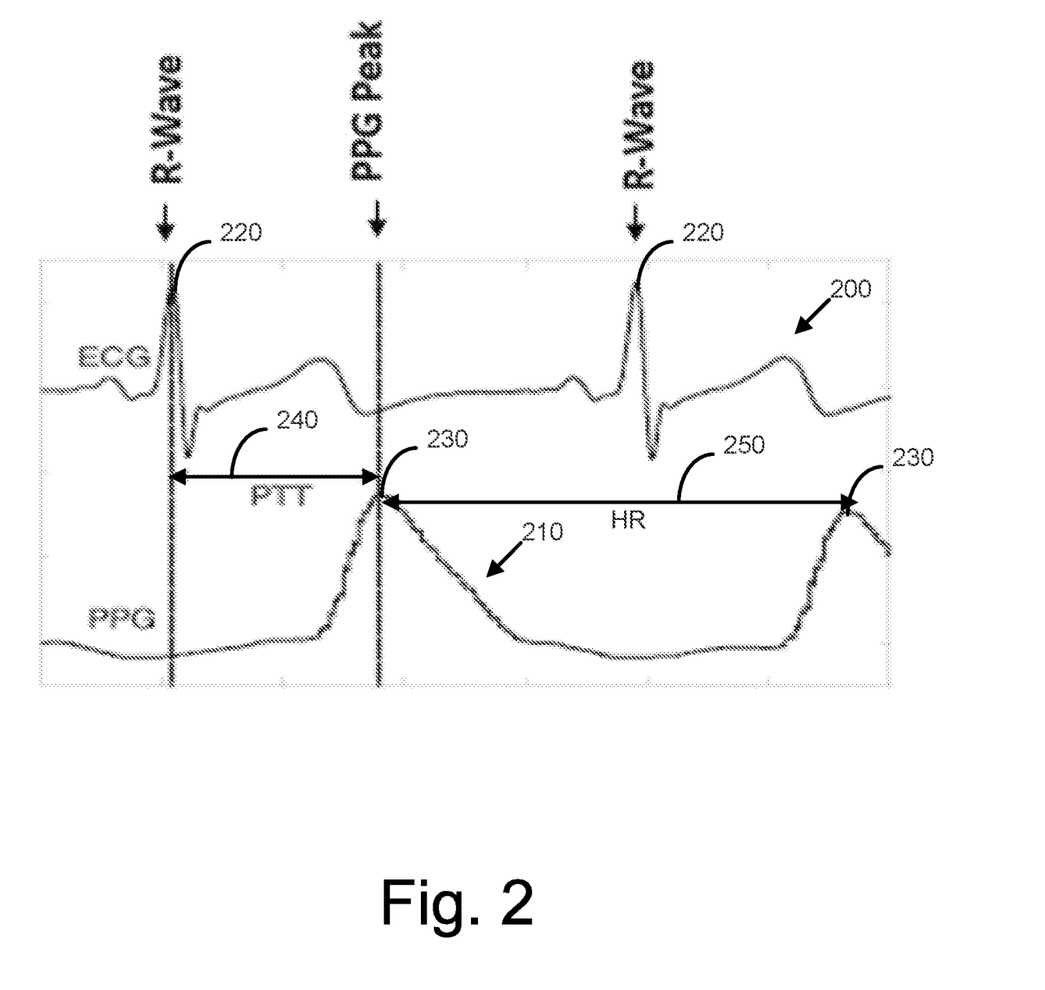
FIG. 2 is a graph illustrating an example ECG signal with respect to a simultaneous PPG signal.

FIG. 2 is a graph illustrating an example ECG signal 200 with respect to a simultaneous PPG signal 210, as may be measured by ECG signal sensor 115 and PPG sensor 120, respectively. ECG signal 200 is illustrated with a conventional ECG wave structure that may include a significant or dominant recurring feature or peak, which may be referred to as R-wave 220. Similarly, PPG signal 210 is illustrated with a conventional PPG wave structure that may include a significant or dominant recurring feature or peak, which may be referred to as PPG peak 230. Also illustrated is a pulse transit time (PTT) 240, which may be a time interval between a R-wave 220 and a next successive PPG peak 230 and may correspond to a blood volume pulse wave to arrive at the blood vessels following a heart contraction that may be represented by R-wave 220.

In embodiments, such as in which ECG contacts 130 and light source 140 and one or more light sensors 145 of PPG sensor 120 may be in engagement with a subject's chest, PPT 240 may be the time interval for a blood volume pulse wave to arrive at the blood vessels on the chest after the heart contracts, as represented by R-wave 220. Blood Pressure (BP) may be inversely proportional to PTT 240, so that determination of PTT 240 may provide an indication of blood pressure. Also illustrated is a heart rate interval 250, a time interval between successive PPG peaks 230, which may correspond to successive heart contractions and may be inversely related to heart rate (HR).

Figure 3:
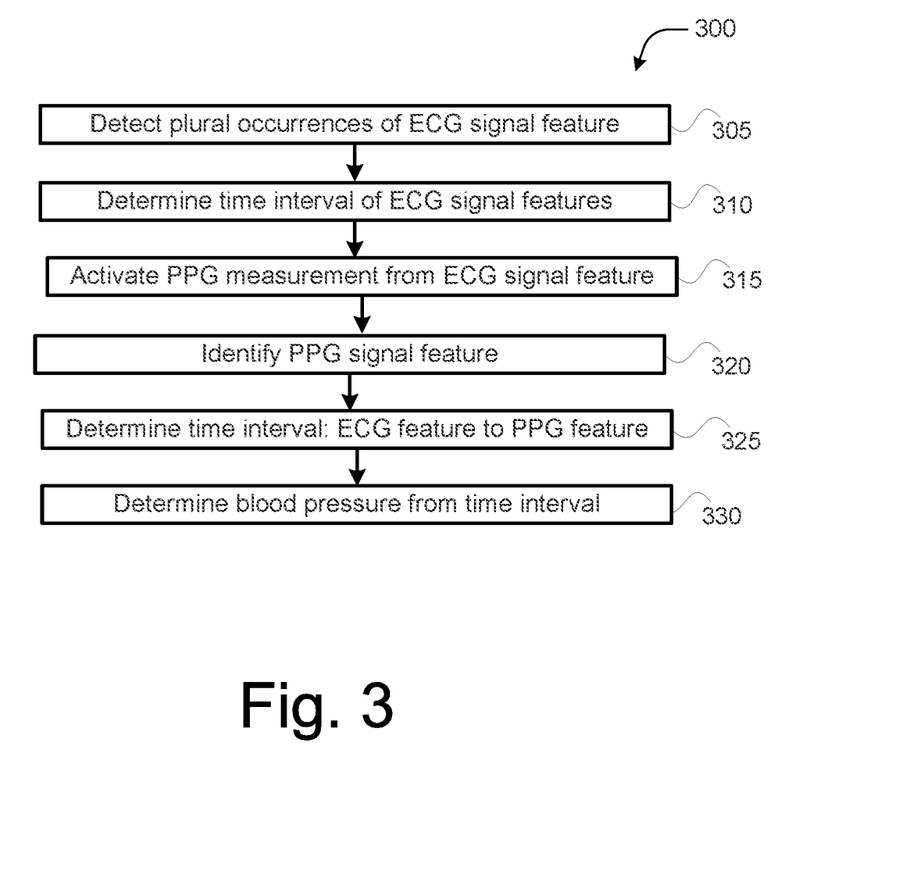
FIG. 3 is a flow flowchart illustrating an example process of monitoring circulatory health, which may include blood pressure and/or heart rate, according to some embodiments.

FIG. 3 is a flow flowchart illustrating an example process 300 of monitoring circulatory health, which may include blood pressure and/or heart rate, according to some embodiments. For illustrative purposes, the operations of process 300 will be described as being performed by blood pressure monitor device 100 (FIG. 1). However, it should be noted that other devices may operate the process 300 or portions of it, including heart rate monitors without blood pressure measurement. While particular examples and orders of operations are illustrated in FIG. 3, in various embodiments, these operations may be re-ordered, separated into additional operations, combined, or omitted altogether.

At operation 305, plural successive occurrences of a signal feature of an ECG signal of a subject may be detected. The signal feature of an ECG signal may be referred to as a detected signal feature. In embodiments, ECG signal sensor 115 may detect plural successive occurrences of an R-wave 220 of an ECG signal 200.

At operation 310, a time interval between the successive occurrences of the ECG signal feature may be determined. In embodiments, the time interval between plural successive occurrences of the R-wave 220 of the ECG signal 200 may be determined and may correspond to a heart-rate (HR) interval. The HR interval may be inversely proportional to an HR for the subject and in embodiments may be indicated in milliseconds (mS).

At operation 315, a PPG measurement of the subject may be activated in relation to the detected signal feature of the ECG signal. In embodiments, PPG sensor 120 may be activated a delay time period T1 after the detected signal feature. For example, the PPG measurement of the subject may be activated for a measurement time period W1, and the PPG measurement of the subject for the measurement time period W1 after the delay time period T1 may include measurement of a PPG signal feature such as a PPG peak 230. An aspect of the PPG measurement of the subject being activated for a measurement time period W1, and after the delay time period T1, is that activation times of the one or more light sources (LEDs) 140 of PPG sensor 120 may be reduced and, as a result, power usage by and heating of LEDs 140 may also be reduced. As a result, activation of the PPG measurement based on the detected signal feature of the ECG signal may reduce power usage by and heating of LEDs 140.

At operation 320, the PPG signal feature of the PPG signal may be identified within the W1 measurement time period. In embodiments, the PPG signal feature may include a PPG peak 230.

At operation 325, a time interval may be determined between the ECG signal feature and the PPG signal feature. In embodiments, the time interval may be a PTT 240 between R-wave 240 of ECG signal 200 and PPG peak 230 of PPG signal 210.

At operation 330, blood pressure (BP) may be determined with respect to the time interval between the ECG signal feature and the PPG signal feature. In embodiments, the BP may be determined with respect to an inverse of PTT 240 between R-wave 240 of ECG signal 200 and PPG peak 230 of PPG signal 210.

In embodiments, operation 325 may return to operation 305, and operations 305-325 may be repeated and may provide plural BP determinations, which may in some embodiments be averaged and/or in other embodiments may be tracked over time and may identify changes, or absence of changes, in the blood pressure determinations. In some embodiments, the time interval between plural successive occurrences of the PPG peak 230 of the PPG signal 210 may be determined and may be designated as corresponding to a HR interval. The HR interval may be inversely proportional to an HR for the subject. In embodiments, an HR for the subject may be determined from one or more HR intervals, which may be based on plural successive occurrences of the PPG peak 230 of the PPG signal 210 and/or may be based on plural successive occurrences of the R-wave 220 of the ECG signal 200.

The accuracy of BP determination may relate to accuracy of PTT determination and/or measurement, which may relate to measuring accurately the time interval between R-wave peaks 220 in ECG signal 200 and following PPG peaks 230 in PPG signal 210. Similarly, HR accuracy may relate to measuring accurately the HR interval between successive PPG peaks 230, for example. Accurate determination of BP and/or HR may relate to accurate identification of PPG peaks 230.

For example, a common PTT value for human subjects at rest may be about 200 milliseconds (mS). An error of 1 mS in PTT determination can cause an error of 1 mm Hg in BP determination. Accurate determination of PTT, such as with less than 5 mS error, may provide for BP error of less than 5 mmHg, which may be a BP error limit in some embodiments.

By some considerations, a sampling rate for ECG signal 200 and PPG signal 210 may be greater than 1000 Hz, so that the consecutive samples may be spaced less than 1 mS apart and any error in PTT determination may be less than 1 mS. For the PPG measurement, the one or more LEDs 140 of PPG sensor 120 may be operated (e.g., activated/deactivated, or turned ON/OFF, or pulsed) each 1 mS for each PPG sample measurement. In some embodiments, LEDs 140 may be pulsed at up to 100 mA peak current, for example, to measure PPG signal 210 on some skin tones. However, pulsation of LEDs 140 at a frequency of about 1000 Hz and high peak current may cause significant drain of a battery power supply. In some embodiments, such pulsation of LEDs 140 may also cause significant heating of LEDs 140, which can result in skin burns for a subject.

Embodiments may be directed to reduced power usage by and heating of LEDs 140. Some embodiments may employ reduced or lower sampling rates (e.g., in a range of about 100 Hz) to reduce power usage by and heating of LEDs 140. However, a sampling rate of 100 Hz may provide PPG samples that may be 10 mS apart, which may cause significant errors in PTT and HR determination.

Figure 4:
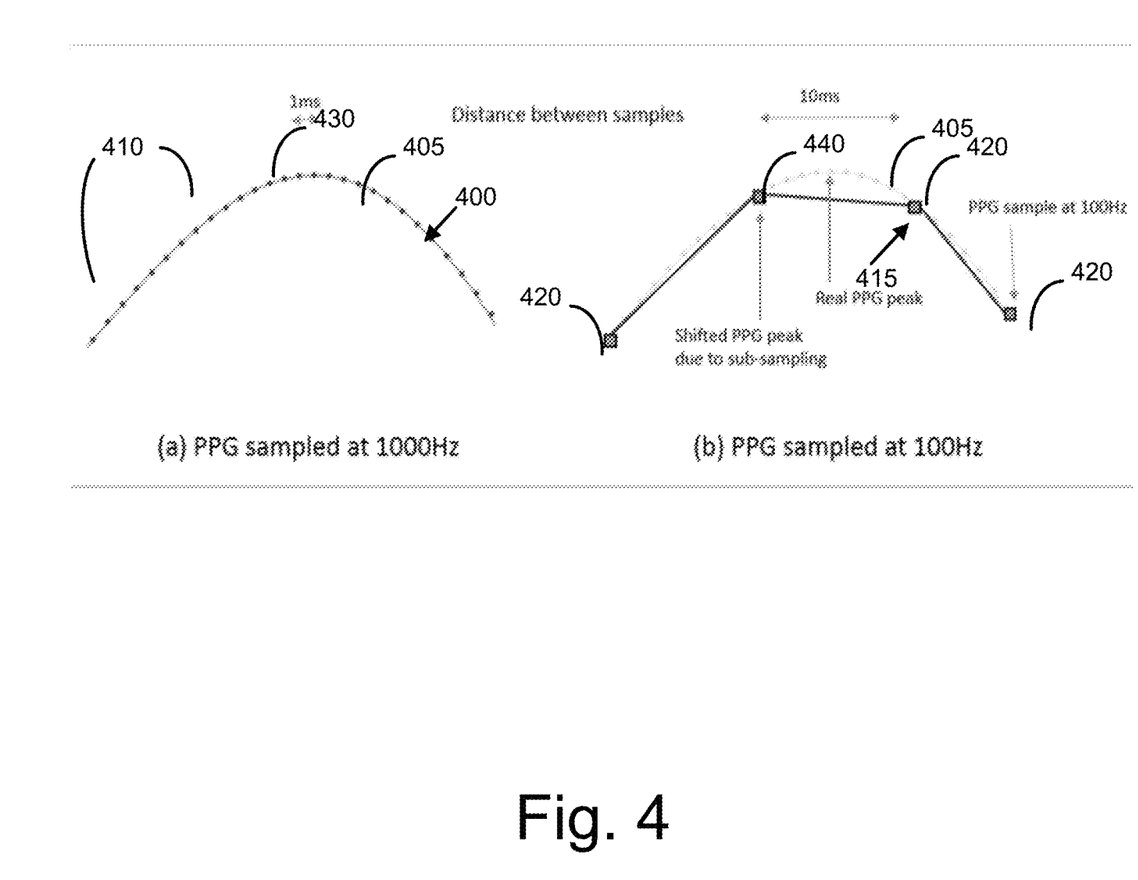
FIG. 4 is an illustration of a graph representing sampling of an example PPG signal.

FIG. 4 is an illustration of a graph 400 representing sampling of an example PPG signal 405 with samples 410 at a sampling interval of 1 mS (e.g., a sampling rate of 1000 Hz) and a graph 415 representing sampling of example PPG signal 405 at a sampling interval of 10 mS (e.g., a sampling rate of 100 Hz) with samples 420. The sampling interval of 1 mS in graph 400 may identify in PPG signal 410 a PPG peak 430 with sufficient accuracy (e.g., a time interval error of less than 1 mS) to meet BP determination standards. In contrast, the sampling interval of 10 mS in graph 415 may identify in PPG signal 410 a PPG peak 440 that may be inaccurate by a time interval error of 4-5 mS, which may introduce an unacceptable error into a BP and/or HR determination.

Sampling intervals of more than 1 mS, such as the sampling interval of 10 mS, may be referred to as sub-sampling of PPG signal 405 or sampling of PPG signal 405 at a sub-sample resolution. Sampling intervals of about 1 mS or less, or which can identify a PPG peak with sufficient accuracy for acceptable BP and/or HR determination, may be referred to as sampling of PPG signal 405 at a sample resolution.

Figure 5:
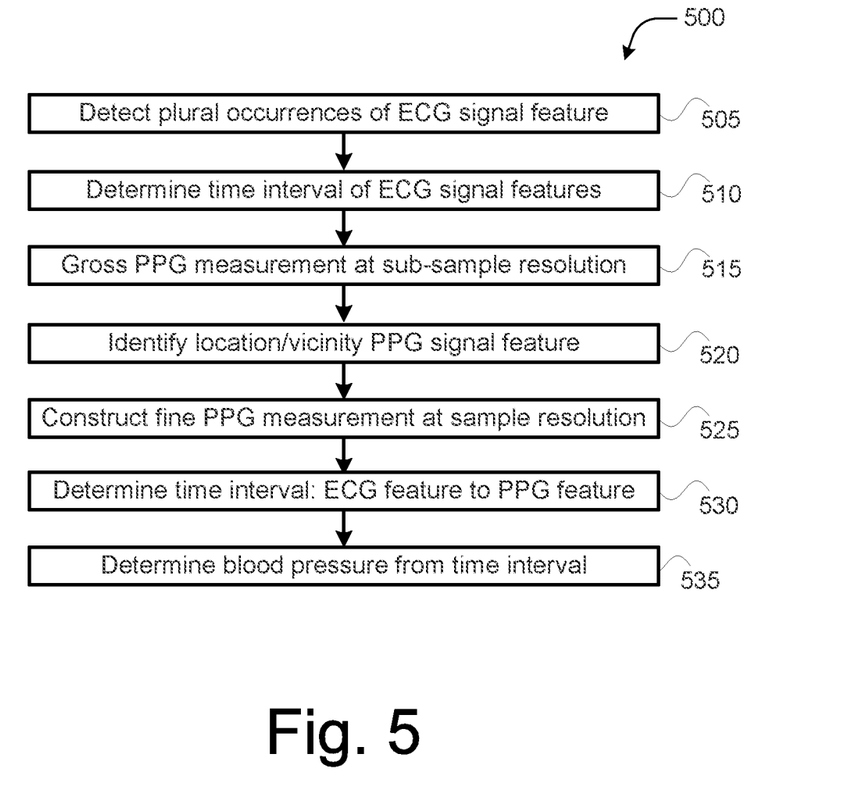
FIG. 5 is a flow flowchart illustrating an example process of monitoring circulatory health, which may include blood pressure and/or heart rate, according to some embodiments.

FIG. 5 is a flow flowchart illustrating an example process 500 of monitoring circulatory health, which may include blood pressure and/or heart rate, according to some embodiments. Process 500 may provide accurate determination of BP and/or HR with reduced power usage by and/or heating of light sources and or LEDs in a PPG sensor. In some embodiments, process 500 may employ activation of sampling of a PPG signal based on a signal feature (e.g., R-wave) of an ECG signal, wherein an initial sampling of the PPG signal at a sub-sampling resolution may identify a location or vicinity of the PPG peak. The PPG signal may be mathematically reconstructed (sometimes referred to as constructed) at the location or vicinity of the PPG peak at a sampling resolution, and the PPG peak may be identified and/or determined with sufficient accuracy from the constructed PPG signal.

For illustrative purposes, the operations of process 500 will be described as being performed by blood pressure monitor device 100 (FIG. 1). However, it should be noted that other devices may operate the process 500. While particular examples and orders of operations are illustrated in FIG. 5, in various embodiments, these operations may be re-ordered, separated into additional operations, combined, or omitted altogether.

At operation 505, plural successive occurrences of a signal feature of an ECG signal of a subject may be detected. The signal feature of an ECG signal may be referred to as a detected signal feature. In embodiments, ECG signal sensor 115 may detect plural successive occurrences of an R-wave 220 of an ECG signal 210. In some embodiments, ECG signal sensor 115 may be operated substantially continuously without significant adverse effect on power supply (e.g., battery) resources and/or comfort or safety of the patient or subject.

At operation 510, a time interval between the successive occurrences of the ECG signal feature may be determined. In embodiments, the time interval between plural successive occurrences of the R-wave 220 of the ECG signal 210 may be determined and may correspond to a heart-rate (HR) interval. The HR interval may be inversely proportional to a HR for the subject and in embodiments may be indicated in milliseconds (mS).

At operation 515, an initial or gross PPG measurement of the subject at a sub-sample resolution may be activated in relation to the detected signal feature of the ECG signal. In embodiments, light source and/or LED 140 of PPG sensor 120 may be activated at the sub-sample resolution after a delay time period T1 following the detected signal feature. For example, the PPG measurement of the subject may be activated for a measurement time period W1, and the PPG measurement of the subject for the measurement time period W1 after the delay time period T1 may include measurement of a PPG signal feature such as a PPG peak 230. In embodiments, the sub-sample resolution may include a sample time interval of 10 mS, for example, and light source and/or LED 140 of PPG sensor 120 may remain off or deactivated except during the measurement time period W1.

At operation 520, a location or vicinity of the PPG signal feature (e.g., PPG peak 230) may be identified and/or determined from the initial or gross PPG measurement. In embodiments, the location or vicinity of the PPG signal feature may include a selected number (e.g., three or more) of gross PPG measurements that may precede and a selected number (e.g., three or more) of gross PPG measurements that may follow an apparent PPG signal feature in the gross PPG measurement.

At operation 525, a subsequent or fine PPG measurement of the subject at a sample resolution may be constructed and/or reconstructed (e.g., mathematically) in relation to the detected signal feature of the ECG signal at the PPG signal feature location or vicinity identified and/or determined from the initial or gross PPG measurement. Constructing or reconstructing the PPG signal feature may include curve fitting information from the initial or gross PPG measurement. The curve fitting may employ local polynomial regression based curve-fitting that, in some embodiments, may include local polynomial regression based curve-fitting that may use a least squares approximation to plot a smooth curve between the sub-sample resolution data near and/or in the vicinity of the PPG peak. (Polynomial regression is a statistical technique used to fit a curve between a set of points.) The equation of the curve y through a set of points may be modeled as an $n^{th}$ degree polynomial, so as to minimize least-squares error:

$$y = a_0 + a_1 x + a_2 x^2 + a_3 x^3 + \ldots + a_n x^n + \varepsilon|$$

For example, embodiments may employ a 5th degree polynomial for curve fitting to identify with sufficient accuracy a temporal location or vicinity of the PPG peak with minimal computational complexity. In embodiments, coefficients of the equation of the polynomial curve may be determined by numerical methods, and the equation may be used to reconstruct a segment of curve around the gross-level PPG peak at a sample resolution frequency of 1000 Hz, for example, to identify a location or vicinity of the PPG for subsequent or fine PPG measurement.

At operation 530, a time interval may be determined between the ECG signal feature and the PPG signal feature in the constructed PPG measurement at a sample resolution. In embodiments, the time interval may be a PTT 240 between R-wave 240 of ECG signal 210 and PPG peak 230 of PPG signal 210.

At operation 535, blood pressure may be determined with respect to the time interval between the ECG signal feature and the PPG signal feature. In embodiments, the blood pressure may be determined with respect to an inverse of PTT 240 between R-wave 240 of ECG signal 210 and PPG peak 230 of PPG signal 210.

In embodiments, operation 535 may return to operation 505, and operations 505-525 may be repeated and may provide plural blood pressure determinations, which may in some embodiments be averaged and/or in other embodiments may be tracked over time and may identify changes, or absence of changes, in the blood pressure determinations. In other embodiments, the time interval between plural successive occurrences of the PPG peak 230 of the ECG signal 210 may be determined and may correspond to a heart-rate (HR) interval. The HR interval may be inversely proportional to a HR for the subject and in embodiments may be indicated in milliseconds (mS).

Figure 6:
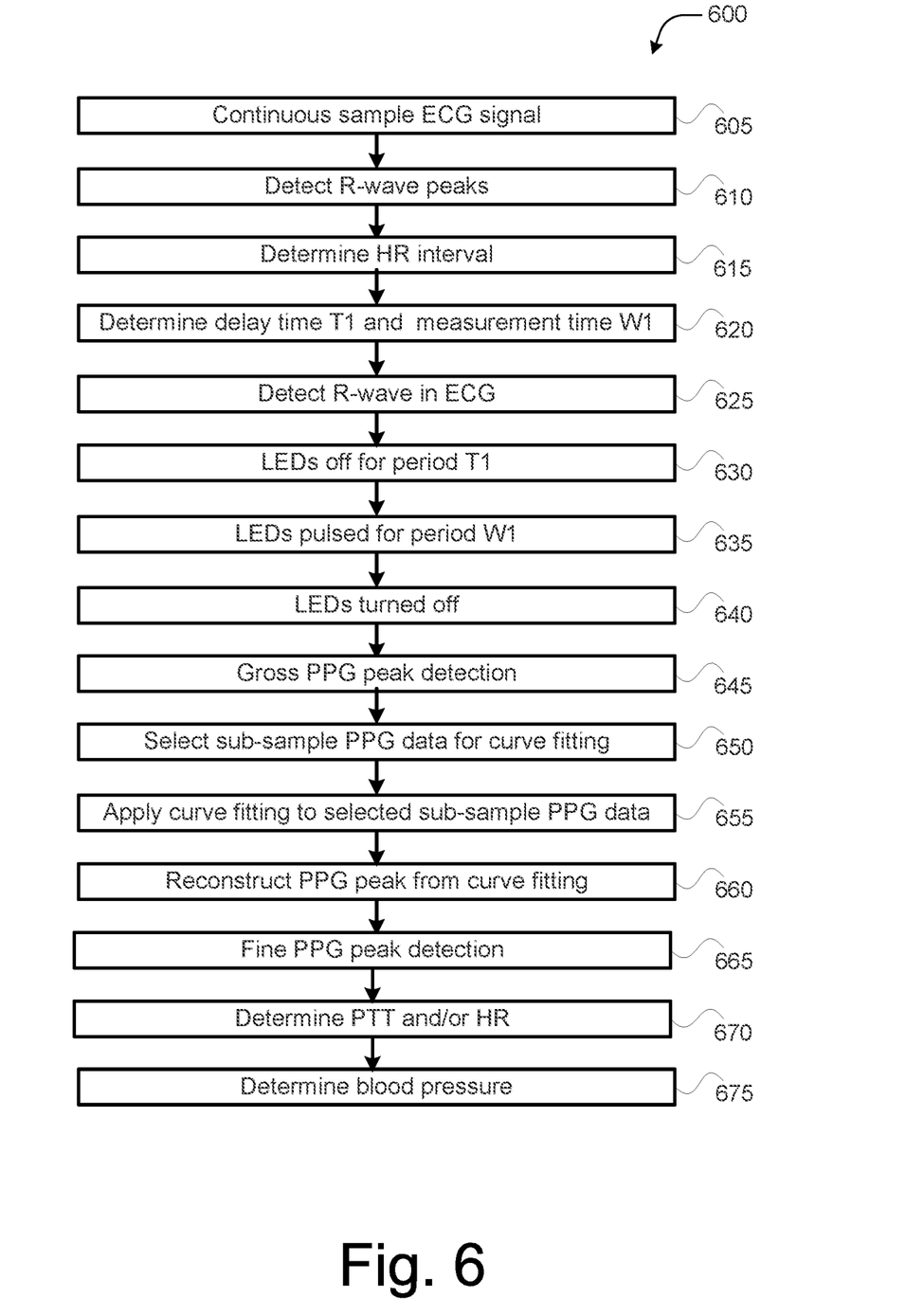
FIG. 6 is a flow flowchart illustrating an example process of monitoring circulatory health, which may include blood pressure and/or heart rate, according to some embodiments.

FIG. 6 is a flow flowchart illustrating an example process 600 of monitoring circulatory health, which may include blood pressure and/or heart rate, according to some embodiments. Process 600 may provide accurate determination of BP and/or HR with reduced power usage by and/or heating of light sources and or LEDs in a PPG sensor.

At operation 605, ECG signal of a subject patient may be continuously sampled. In embodiments, LEDs 140 of PPG sensor 120 may generally remain off.

At operation 610, R-wave peaks may be detected from the ECG signal.

At operation 615, an HR interval may be determined between R-wave peaks from the ECG signal.

At operation 620, a delay time period T1 and a measurement time period W1 may be determined from the HR interval. For example, the PPG measurement of the subject may be activated for the measurement time period W1 after the delay time period T1 following an R-wave peak. As described, ECG and PPG signals are synchronous, and may relate to blood flow to peripheral blood vessels (e.g., PPG peak) following a heart contraction (e.g., R-wave in ECG signal) Hunman subject or patients may have a physiological HR range of 30 to 240 beats per minute (bpm). For example, a HR of 60 bpm has a HR interval of 1000 ms, and the PPG peak may lag the R-wave by about 200 mS. In embodiments, the delay time period T1 may be set as a function of the HR interval as follows:

$$T1 = 0.15 * HR \text{ interval (in milliseconds)}$$

Hence, with an example HR of 60 bpm (HR interval of 1000 mS), delay time period T1 may be 150 mS, and with an example HR of 120 bpm (HR interval=500 mS), delay time period T1 may be 75 mS. The measurement time period W1 also may be determined with respect to HR interval and physiological limits within the HR range of 30 to 240 bpm. IN embodiments, the measurement time period W1 may be set as:

$$W1 = 0.2 * HR \text{ interval (in milliseconds)}$$

Hence, at an example HR of 60 bpm (HR interval=1000 mS), the measurement time period W1 may be set as 200 mS.

At operation 625, an R-wave is detected in the ECG signal.

At operation 630, LEDs 140 of PPG sensor 120 remain off for the delay time period T1 following the R-wave in the ECG signal.

At operation 635, LEDs 140 of PPG sensor 120 are pulsed at a sub-sample resolution rate (e.g., 100 Hz) for the measurement time period W1 to obtain a sub-sampled PPG measurement.

At operation 640, LEDs 140 of PPG sensor 120 are turned off after the measurement time period W1.

At operation 645, an initial or gross PPG peak detection may be performed with respect to the sub-sampled PPG measurement. In embodiments, the initial or gross PPG peak detection may identify a temporal location or vicinity of a gross-level PPG peak.

At operation 650, data from the sub-sampled PPG measurement may be selected for curve-fitting. In embodiments, a number of data measurements (e.g., three) before and after an apparent PPG peak in the sub-sampled PPG measurement may be selected.

At operation 655, curve-fitting may be applied to the number of data measurements. In embodiments, local polynomial regression-based curve fitting may be applied and may determine a polynomial function fitting the data measurements.

At operation 660, a PPG peak may be reconstructed mathematically at a sampling resolution (e.g., 1000 Hz) based on the polynomial function fitting the data measurements.

At operation 665, a subsequent or fine PPG peak detection may be performed with a sample resolution with respect to the mathematically reconstructed PPG measurement. In embodiments, the subsequent or fine PPG peak detection may identify the PPG peak with sampling resolution or accuracy.

At operation 670, PTT and/or HR may be determined from the subsequent or fine PPG peak detection.

At operation 675, BP may be determined from the PTT.

Embodiments described herein may include equidistant sub-sampling (e.g., samples are temporally equidistant), which may be coupled with computationally light-weight curve-fitting to reconstruct a PPG peak at a fine-grained resolution. As a result, embodiments may be employed on or in association on resource-constrained, low-compute, low-power wearable processors. Embodiments utilize aspects of sampling rate, LED power dissipation for PPG measurement, and HR/PTT accuracy to achieve accurate measure with reduced power dissipation and risk of injury. In contrast, other implementations may require significantly higher computation-intensive reconstruction algorithms, which may be beyond processing capabilities of wearable processors.

In comparison to implementations with continuous LED excitation for PPG measurement, embodiments described herein, with R-wave synchronized LED excitation for PPG measurement can provide up to 5× reduction in LED power overall. Such reduction in power may include sub-sampling PPG at 100 Hz, with a 10× LED power/LED temperature reduction, and curve-fitting on sub-sampled PPG to provide accurate determination of the PPG peak without loss of accuracy. Accordingly, embodiments with ECG-based PPG measurement, sub-sampled LED excitation for PPG measurement, and curve-fitting for sample resolution measurement may obtain the product of 5× reduction in LED power and 10× LED power reduction for an overall reduction in LED power of 50×, relative to continuous LED operation in PPG measurement at sample resolution.

Embodiments of the present disclosure may be implemented into a system using any suitable hardware and/or software to operate as described. In embodiments, controller 110 may include a computing device that may include a number of components, including but not limited to a processor. The processor may include one or more processor cores and/or a hardware accelerator (e.g., FPGA). Controller 110 may further include, but is not limited to, volatile memory (e.g., DRAM), non-volatile memory (e.g., ROM), and flash memory. In embodiments, the flash memory and/or ROM may include executable programming instructions configured to implement operations of controller 110. In embodiments, some of the described operations of controller 110 may be implemented with the hardware accelerator instead. Controller 110 may include one or more communication chips that may be dedicated to wired communications or shorter range wireless communications such as Wi-Fi and Bluetooth. The processor and/or the computing device may include a die in a package assembly. The term "processor" may refer to any device or portion of a device that processes electronic data from registers and/or memory to transform that electronic data into other electronic data that may be stored in registers and/or memory.

Some non-limiting Examples are provided below.

Example 1 may include a blood pressure monitor device, which may comprise: an electrocardiographic (ECG) signal sensor to detect a detected signal feature of an ECG signal of a subject; and a controller coupled to the ECG signal sensor to activate at a sub-sample resolution photoplethysmographic (PPG) measurement of the subject in relation to the detected signal feature; wherein the controller is further to identify a PPG signal feature location in the PPG measurement at the sub-sample resolution; and the controller is further to activate at a sample resolution PPG measurement of the subject at the PPG signal feature location to identify the PPG signal feature.

Example 2 may include the device of example 1, wherein the sub-sample resolution PPG measurement may be activated for a time-limited period.

Example 3 may include the device of example 1 or 2 wherein the detected signal feature of the ECG signal may include an ECG R-wave.

Example 4 may include the device of example 1 or 2 wherein the PPG signal feature may include a PPG signal peak.

Example 5 may include the device of example 1 or 2 wherein the controller may further apply curve-fitting to the PPG measurement at the sub-sample resolution to construct the sample resolution PPG measurement of the subject at the PPG signal feature location.

Example 6 may include the device of example 5 wherein the controller may further apply polynomial regression curve-fitting.

Example 7 may include the device of example 1 or 2 wherein the device may be included as part of a wearable device.

Example 8 may include the device of example 7 wherein the device may be included as part of a cuffless wearable device.

Example 9 may include a wearable blood pressure monitor device, which may comprise: one or more electrocardiographic (ECG) signal sensors; one or more photoplethysmographic (PPG) sensors; and a controller coupled to the one or more ECG signal sensors and the one or more PPG sensors, wherein the controller is to: direct the one or more ECG signal sensors detect a selected signal feature of an ECG signal of a subject; direct the one or more PPG sensors to activate at a sub-sample resolution PPG measurement of the subject in relation to the selected signal feature for a time-limited period; identify a PPG signal feature location in the PPG measurement at the sub-sample resolution; and construct at a sample resolution PPG measurement of the subject at the PPG signal feature location to identify the PPG signal feature.

Example 10 may include the device of example 9 wherein the detected signal feature of the ECG signal may include an ECG R-wave.

Example 11 may include the device of example 9 wherein the PPG signal feature may include a PPG signal peak.

Example 12 may include the device of example any of examples 9-11 wherein the controller may further apply curve-fitting to the PPG measurement at the sub-sample resolution to identify the PPG signal feature location in the PPG measurement at the sub-sample resolution.

Example 13 may include the device of example 12 wherein the controller may further to apply polynomial regression curve-fitting.

Example 14 may include the device of any of examples 9-11 wherein the device may be included as part of a cuffless blood pressure patch.

Example 15 may include a wearable health data monitor device, which may comprise: one or more photoplethysmographic (PPG) sensors; a controller coupled to the one or more PPG sensors, wherein the controller is to: activate at a sub-sample resolution a time-limited PPG measurement of a subject in relation to a selected signal feature; identify a PPG signal feature location in the PPG measurement at the sub-sample resolution; and construct at a sample resolution a PPG measurement of the subject at the PPG signal feature location to identify the PPG signal feature; and a body to host the one or more PPG sensors and the controller, wherein in body is wearable by the subject.

Example 16 may include the device of example 15 wherein the PPG signal feature may include a PPG signal peak.

Example 17 may include the device of example 15 wherein the controller may further apply curve-fitting to the PPG measurement at the sub-sample resolution to identify the PPG signal feature location in the PPG measurement at the sub-sample resolution.

Example 18 may include the device of example 17 wherein the controller may further apply polynomial regression curve-fitting.

Example 19 may include the device of any of examples 15-18 wherein the device may be included as part of a cuffless wearable device.

Example 20 may include the device of any of examples 15-18 wherein the device may be included as part of a wearable heart-rate monitor.

Example 21 may include the device of any of examples 15-18, wherein the device may further include one or more electrocardiographic (ECG) signal sensors and the controller may further detect the selected signal feature from an ECG signal of the subject.

Example 22 may include the device of example 21 wherein the device may be included as part of a wearable blood pressure monitor.

Example 23 may include at least one computer-readable storage medium having a plurality of instructions, in response to execution by a processor of a wearable health data monitor, cause the wearable health data monitor to: activate at a sub-sample resolution photoplethysmographic (PPG) measurement of the subject in relation to a selected signal feature; identify a PPG signal feature location in the PPG measurement at the sub-sample resolution; and construct at a sample resolution PPG measurement of the subject at the PPG signal feature location to identify the PPG signal feature.

Example 24 may include the at least one computer-readable storage medium of of example 23 wherein the sub-sample resolution PPG measurement may be activated for a time-limited period.

Example 25 may include the at least one computer-readable storage medium of example 23 wherein the PPG signal feature may include a PPG signal peak.

Example 26 may include the at least one computer-readable storage medium of any of examples 23-25 wherein the plurality of instructions may further include instructions, in response to execution by the processor of the wearable health data monitor, cause the wearable health data monitor to apply curve-fitting to the PPG measurement at the sub-sample resolution to identify the PPG signal feature location in the PPG measurement at the sub-sample resolution.

Example 27 may include the at least one computer-readable storage medium of example 26 wherein the curve-fitting may include polynomial regression curve-fitting.

Example 28 may include the at least one computer-readable storage medium of any of examples 23-25 wherein the wearable health data monitor may be included as part of a wearable heart-rate monitor.

Example 29 may include the at least one computer-readable storage medium of any of examples 23-25 wherein the plurality of instructions may further include instructions, in response to execution by the processor of the wearable health data monitor, cause the wearable health data monitor to detect the selected signal feature as a detected signal feature of an electrocardiographic (ECG) signal of the subject.

Example 30 may include the at least one computer-readable storage medium of example 29 wherein the detected signal feature of the ECG signal may include an ECG R-wave.

Example 31 may include the at least one computer-readable storage medium of example 29 wherein the wearable health data monitor may be included as part of a cuffless blood pressure monitor device.

Example 32 may include a method, which may comprising: detecting with one or more electrocardiographic (ECG) signal sensors a selected signal feature of an ECG signal of a subject; activating one or more photoplethysmographic (PPG) sensors at a sub-sample resolution PPG measurement of the subject in relation to the selected signal feature; identifying a PPG signal feature location in the PPG measurement at the sub-sample resolution; and constructing at a sample resolution PPG measurement of the subject at the PPG signal feature location to identify the PPG signal feature.

Example 33 may include the method of example 32 wherein the detected signal feature of the ECG signal may include an ECG R-wave.

Example 34 may include the method of example 32 wherein the PPG signal feature may include a PPG signal peak.

Example 35 may include the method of any of examples 32-34 wherein the method may further comprise applying curve-fitting to the PPG measurement at the sub-sample resolution to identify the PPG signal feature location in the PPG measurement at the sub-sample resolution.

Example 36 may include the method of example 35 wherein the curve-fitting may include polynomial regression curve-fitting.

Example 37 may include the method of any of examples 32-34 wherein the method may be performed by a cuffless blood pressure patch.

Example 38 may include the method of any of examples 32-34 wherein the method may include activating the one or more PPG sensors at the sub-sample resolution PPG measurement of the subject in relation to the selected signal feature for a time limited period.

Example 39 may include an apparatus, which may comprise: means to detect a selected signal feature of an electrocardiographic (ECG) signal of a subject; means to activate at a sub-sample resolution a photoplethysmographic (PPG) measurement of the subject in relation to the selected signal feature; means to identify a PPG signal feature location in the PPG measurement at the sub-sample resolution; and means to construct at a sample resolution PPG measurement of the subject at the PPG signal feature location to identify the PPG signal feature.

Example 40 may include the apparatus of example 39 wherein the detected signal feature of the ECG signal may include an ECG R-wave.

Example 41 may include the apparatus of example 39 wherein the PPG signal feature may include a PPG signal peak.

Example 42 may include the apparatus of any of examples 39-41 wherein the apparatus may further comprise means to apply curve-fitting to the PPG measurement at the sub-sample resolution to identify the PPG signal feature location in the PPG measurement at the sub-sample resolution.

Example 43 may include the apparatus of example 42 wherein the curve-fitting may include polynomial regression curve-fitting.

Example 44 may include the apparatus of any of examples 39-41 wherein the apparatus may be included in a cuffless blood pressure patch.

Example 45 may include the apparatus of any of examples 39-41 wherein the apparatus may include means to activate the PPG measurement at the sub-sample resolution in relation to the selected signal feature for a time limited period.

Although certain embodiments have been illustrated and described herein for purposes of description, a wide variety of alternate and/or equivalent embodiments or implementations calculated to achieve the same purposes may be substituted for the embodiments shown and described without departing from the scope of the present disclosure. This application is intended to cover any adaptations or variations of the embodiments discussed herein, limited only by the claims.

What is claimed:

1. A blood pressure monitor device, comprising:
   an electrocardiographic (ECG) signal sensor to detect a detected signal feature of an ECG signal of a subject;
   a photoplethysmographic (PPG) sensor to perform PPG measurement of the subject; and
   a controller coupled to the ECG signal sensor and the PPG sensor to activate the PPG sensor to perform PPG measurement of the subject in response to a detection of the detected signal feature of the ECG signal of the subject, the PPG sensor being activated to perform the PPG measurement of the subject at a first sampling resolution that is less frequent than a second sampling resolution;
   wherein the controller is further to identify one or more initial PPG signal features and their locations in the PPG measurement performed at the first sampling resolution; and to infer a final PPG signal feature and its location as if the PPG measurement of the subject had been performed at the more frequent second sampling resolution, using the initial PPG signal features and their locations identified from the PPG measurement of the subject performed at the less frequent first sampling resolution.

2. The device of claim 1, wherein the PPG sensor is activated to perform the PPG measurement of the subject at the first sampling resolution for a time period.

3. The device of claim 1, wherein the detected signal feature of the ECG signal includes an ECG R-wave.

4. The device of claim 1, wherein the initial and final PPG signal features include PPG signal peaks.

5. The device of claim 1, wherein to infer a final PPG signal feature and its location as if the PPG measurement of the subject had been performed at the more frequent second sampling resolution, the controller is to apply curve-fitting to the PPG measurement of the subject performed at the first sampling resolution.

6. The device of claim 5, wherein to apply curve-fitting, the controller is to apply polynomial regression curve-fitting.

7. The device of claim 1, wherein the device is included as part of a wearable device.

8. The device of claim 7, wherein the device is included as part of a cuffless wearable device.

9. A wearable blood pressure monitor device, comprising:
   one or more electrocardiographic (ECG) signal sensors;
   one or more photoplethysmographic (PPG) sensors; and
   a controller coupled to the one or more ECG signal sensors and the one or more PPG sensors, wherein the controller is to:
   direct the one or more ECG signal sensors to detect a selected signal feature of an ECG signal of a subject;
   direct the one or more PPG sensors to activate to perform PPG measurement of the subject for a time period, in response to a detection of the selected signal feature by the one or more ECG signal sensors, the one or more PPG sensor being activated to perform the PPG measurement of the subject at a first sampling resolution that is less frequent than a second sampling resolution;
   identify one or more initial PPG signal features and their locations in the PPG measurement performed at the first sampling resolution; and
   infer a final PPG signal feature and its location as if the PPG measurement of the subject been performed at the more frequent second sampling resolution, using the initial PPG signal features and their locations identified from the PPG measurement of the subject performed at the less frequent first sampling resolution.

10. The device of claim 9, wherein the selected signal feature of the ECG signal includes an ECG R-wave.

11. The device of claim 9, wherein the initial and final PPG signal features include PPG signal peaks.

12. The device of claim 9, wherein to infer a final PPG signal feature and its location as if the PPG measurement of the subject had been performed at the more frequent second sampling resolution, the controller is to apply curve-fitting to the PPG measurement of the subject performed at the first sampling resolution.

13. The device of claim 9 wherein the device is included as part of a cuffless blood pressure patch.

14. A wearable health data monitor device, comprising:
   one or more electrocardiographic (ECG) signal sensors;
   one or more photoplethysmographic (PPG) sensors;
   a controller coupled to the one or more ECG signal sensors and the one or more PPG sensors, wherein the controller is to:

activate the PPG sensors for a time period to perform PPG measurement of a subject in response to a detection of a selected signal feature of an electrocardiographic (ECG) signal of the subject by the one or more ECG signal sensors, the PPG sensor being activated to perform the PPG measurement of the subject at a first sampling resolution that is less frequent than a second sampling resolution;

identify one or more initial PPG signal features and their locations in the PPG measurement performed at the first sampling resolution; and infer a final PPG signal feature and its location as if the PPG measurement of the subject had been performed at the more frequent second sampling resolution, using the initial PPG signal features and their locations identified from the PPG measurement of the subject performed at the less frequent first sampling resolution; and a body to host the one or more PPG sensors and the controller, wherein in body is wearable by the subject.

15. The device of claim 14, wherein the initial and final PPG signal features include PPG signal peaks.

16. The device of claim 14, wherein to infer a final PPG signal feature and its location as if the PPG measurement of the subject had been performed at the more frequent second sampling resolution, the controller is to apply curve-fitting to the PPG measurement of the subject performed at the first sampling resolution.

17. The device of claim 16, wherein to apply curve-fitting the controller is to apply polynomial regression curve-fitting.

18. The device of claim 14, wherein the device is included as part of a cuffless wearable device.

19. The device of claim 14, wherein the device is included as part of a wearable heart-rate monitor.

20. The device of claim 14, wherein the controller is further to detect the selected signal feature from the ECG signal of the subject.

* * * * *